United States Patent
Stchur et al.

(10) Patent No.: US 11,357,522 B2
(45) Date of Patent: Jun. 14, 2022

(54) SURGICAL GLENOID INSTRUMENT SYSTEM

(71) Applicant: Sure Orthopedics LLC, Sarasota, FL (US)

(72) Inventors: Robert Patrick Stchur, Punta Gorda, FL (US); John D. Kuczynski, Sarasota, FL (US)

(73) Assignee: Sure Orthopedics LLC, Sarasota, FL (US)

( * ) Notice: Subject to any disclaimer, the term of this patent is extended or adjusted under 35 U.S.C. 154(b) by 109 days.

(21) Appl. No.: 17/098,143

(22) Filed: Nov. 13, 2020

(65) Prior Publication Data

US 2021/0145498 A1  May 20, 2021

Related U.S. Application Data

(60) Provisional application No. 62/974,106, filed on Nov. 14, 2019.

(51) Int. Cl.
| | | |
|---|---|---|
| *A61B 17/17* | (2006.01) | |
| *A61B 17/02* | (2006.01) | |
| *A61B 17/90* | (2006.01) | |
| *A61B 17/88* | (2006.01) | |
| *A61B 17/16* | (2006.01) | |
| *A61B 17/00* | (2006.01) | |

(52) U.S. Cl.
CPC ...... *A61B 17/1778* (2016.11); *A61B 17/0206* (2013.01); *A61B 17/1684* (2013.01); *A61B 17/8897* (2013.01); *A61B 17/90* (2021.08); *A61B 2017/00477* (2013.01)

(58) Field of Classification Search
CPC ... A61B 17/02; A61B 17/0206; A61B 17/025; A61B 17/1684; A61B 17/17; A61B 17/1778; A61B 17/8897; A61B 17/90
See application file for complete search history.

(56) References Cited

U.S. PATENT DOCUMENTS

| | | | |
|---|---|---|---|
| 5,437,677 A * | 8/1995 | Shearer | A61B 17/1778 606/86 R |
| 7,294,133 B2 * | 11/2007 | Zink | A61B 17/1778 606/96 |

OTHER PUBLICATIONS

"Comprehensive Total Shoulder System: Surgical Technique", Zimmer Biomet, 2018, 56 pages.
"Total Shoulder Arthroplasty System," stryker, 2019, 118 pages.

* cited by examiner

*Primary Examiner* — Larry E Waggle, Jr.
(74) *Attorney, Agent, or Firm* — Kim IP Law Group LLC

(57) ABSTRACT

A surgical instrument system for positioning a guide pin about a glenoid cavity that includes an anterior retractor. The anterior retractor includes a tip structured to engage a scapula, a lateral retractor shaft extending from the tip, and a medial retractor shaft extending substantially transverse from the lateral retractor shaft. The system further includes an alignment guide attachable to the anterior retractor, the alignment guide including an alignment guide shaft, a guide about a distal end of the alignment guide shaft, and a fastener for connecting the alignment guide shaft to the anterior retractor such that a longitudinal axis of the alignment guide shaft is aligned with a longitudinal axis of the medial retractor shaft when fastened thereto.

20 Claims, 19 Drawing Sheets

SURGICAL GLENOID INSTRUMENT SYSTEM

This application claims the benefit of U.S. Provisional Application No. 62/974,106 filed Nov. 14, 2019, entitled "Retractor Based Alignment Guides for Shoulder Arthroplasty Surgery" the entire disclosure of which is incorporated by reference herein in its entirety for all purposes.

BACKGROUND OF THE DISCLOSURE

The exemplary embodiments of the subject disclosure relate generally to a surgical instrument system for positioning a guide pin about a glenoid cavity.

Surgical retractors are used to obtain and maintain access to the anatomy being operated on during a surgical procedure. For most surgeries, several layers of tissue must be dissected through and moved aside (retracted) in order to access the anatomy to perform the operative procedure. It may be necessary to retract soft tissues, such as skin, muscle, fat, and internal organs or bony tissue, or both. While dissecting to reach the surgical site, the surgeon must also avoid damaging certain tissues, such as neural or vascular structures. A retractor system should allow the surgical team to access the surgical site by pushing the tissues aside and holding them in place while doing as little damage as possible to those tissues and also protecting particularly sensitive tissues such as nerves or vascular structures.

Space is an issue when performing an operation, such as a reverse shoulder arthroplasty. Access to the surgical site is limited by soft tissue, bone and also neural and vascular structures that must be protected and avoided. Retractors must be placed and held to access the surgical site, and often an alignment guide must then be placed to perform, for example, initial guide pin placement. In some cases the retractors interfere with other instruments. It is also necessary to control the retractor and the alignment guides separately, sometimes requiring two or more people to hold the retractor(s) and control the instrument being used. There thus remains a need for improved systems for providing retraction while manipulating anatomical parts during operative procedures.

SUMMARY OF THE DISCLOSURE

In accordance with an exemplary embodiment, the subject disclosure provides a surgical instrument system for positioning a guide pin about a glenoid cavity that includes an anterior retractor, and an alignment guide attachable to the anterior retractor. The anterior retractor includes a tip structured to engage a scapula, a lateral retractor shaft extending from the tip, and a medial retractor shaft extending substantially transverse from the lateral retractor shaft. The alignment guide is attachable to the anterior retractor, and includes an alignment guide shaft, a guide about a distal end of the alignment guide shaft, and a fastener for connecting the alignment guide shaft to the anterior retractor such that a longitudinal axis of the alignment guide shaft is aligned with a longitudinal axis of the medial retractor shaft when fastened thereto.

In exemplary embodiments of the subject disclosure, the medial retractor shaft extends from the lateral retractor shaft at an angle of about 90 to about 110 degrees (e.g., 100 degrees). The tip can include a superior flare or curvature. In other exemplary embodiments, the medial retractor shaft extends a length at least twice a length of the lateral retractor shaft.

In alternative embodiments, the medial retractor shaft includes a manual indicia of position along the lateral retractor shaft. The medial retractor shaft can include at least one through hole for engaging the fastener. In an exemplary embodiment, the alignment guide is attachable to medial retractor adjacent a junction of the lateral retractor shaft and the medial retractor shaft.

In exemplary embodiments of the subject disclosure, the lateral retractor shaft includes a marking about an outer periphery a pre-determined distance from the tip corresponding to the distance from an anterior neck of a glenoid to an outer periphery of the glenoid cavity. In other exemplary embodiments, the anterior retractor further comprises a second lateral retractor shaft extending from the medial retractor shaft.

In accordance with another exemplary embodiment, the fastener is a cam lock. According to yet another embodiment, the alignment guide shaft includes at least one through hole with a longitudinal axis therethrough that extends at an angle from about 90 degrees to about 110 degrees from a longitudinal axis of the alignment guide shaft.

In accordance with yet another exemplary embodiment, the guide includes a guide aperture about the distal end of the alignment guide shaft. For example, the guide aperture can extend at an angle of from about 1 degrees to about 20 degrees from a longitudinal axis. A biased detent can also be provided about the guide aperture.

In accordance with yet another exemplary embodiment, the surgical instrument system further includes a guide pin cannula receivable by the guide. The guide pin cannula can include a distal tip that includes a flange, and the flange can extend at an angle of from about from about 5 to about 25 degrees from a plane perpendicular to a guide pin cannula shaft. The guide pin cannula includes a guide pin advanceable therein. Alternatively, the surgical instrument can include a guide insert including an inner aperture sized to receive a guide pin.

BRIEF DESCRIPTION OF THE SEVERAL VIEWS OF THE DRAWINGS

The following detailed description of the exemplary embodiments of the subject disclosure will be better understood when read in conjunction with the appended drawings. For the purpose of illustrating the present disclosure, there is shown in the drawings exemplary embodiments. It should be understood, however, that the subject application is not limited to the precise arrangements and instrumentalities shown.

DETAILED DESCRIPTION OF THE DISCLOSURE

Figure 1:
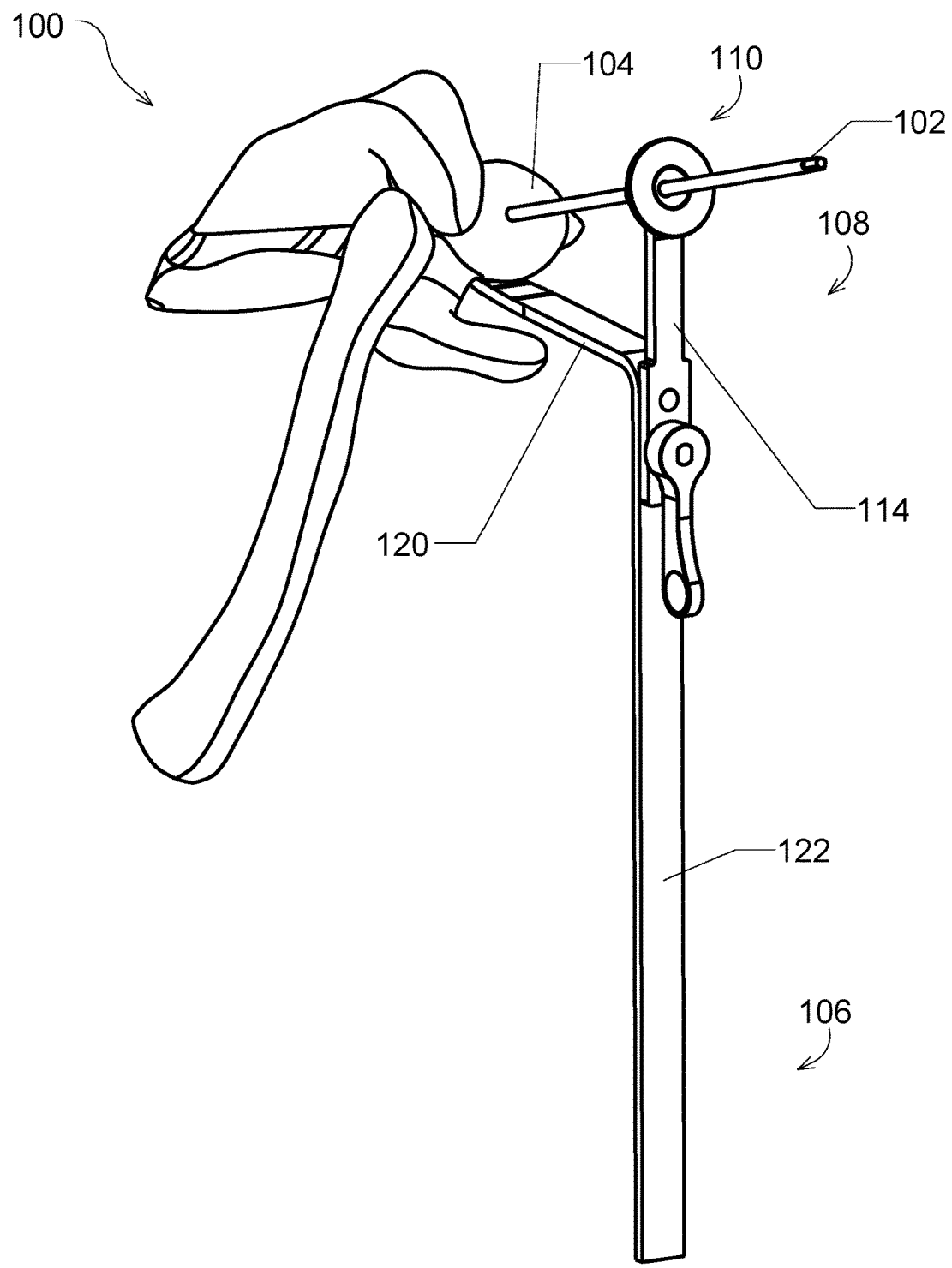
FIG. 1 is a perspective view of a surgical instrument system in accordance with an exemplary embodiment of the subject disclosure.

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

As used herein, the term "adjacent" refers to being near or adjoining. Adjacent components (which can be integral or separate) can be spaced apart from one another, or can be in actual or direct contact with one another (i.e., directly adjacent).

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the drawings, FIGS. 1-14 disclose a surgical instrument system 100 for positioning a guide pin 102 about a glenoid cavity 104 according to an exemplary embodiment of the subject disclosure. The surgical instrument system 100 includes an anterior retractor 106 that includes a tip 116 structured to engage a scapula 118 and an alignment guide 108 attachable to the anterior retractor that includes a guide 110 about a distal end 112 of an alignment guide shaft 114.

Figure 2:
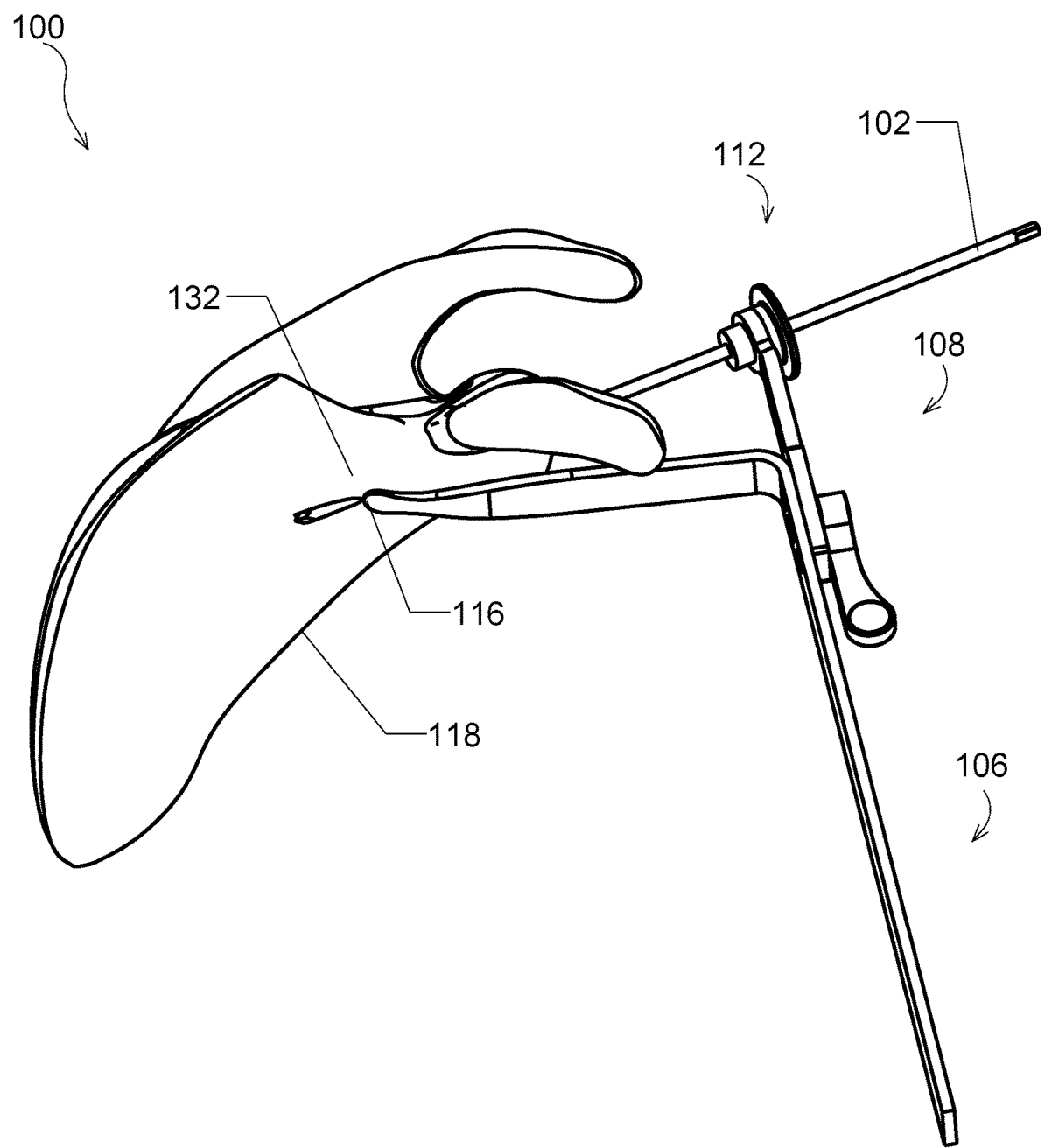
FIG. 2 is an anterior view of the surgical instrument system of FIG. 1.
Figure 3:
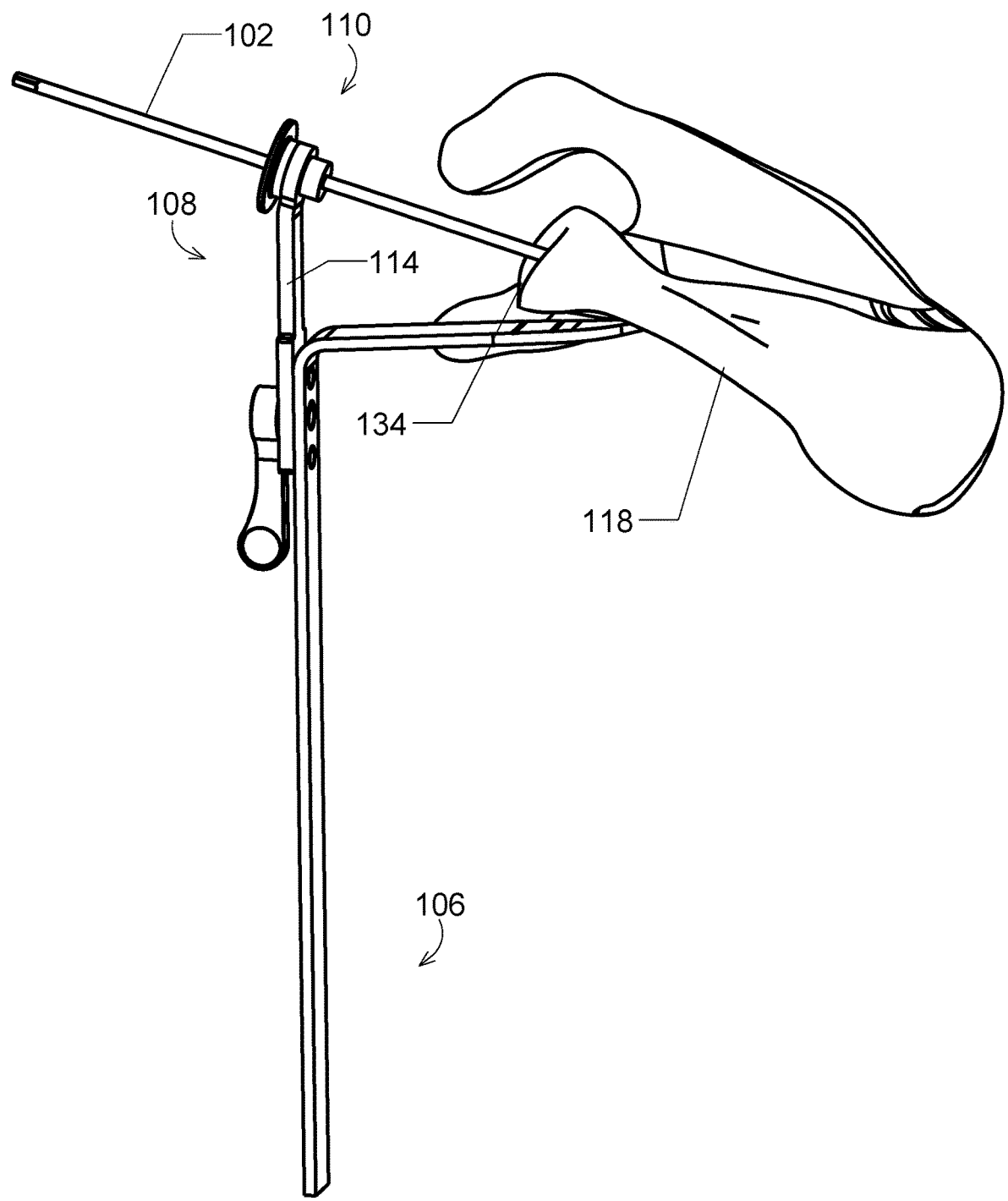
FIG. 3 is a posterior view of the surgical instrument system of FIG. 1.
Figure 4:
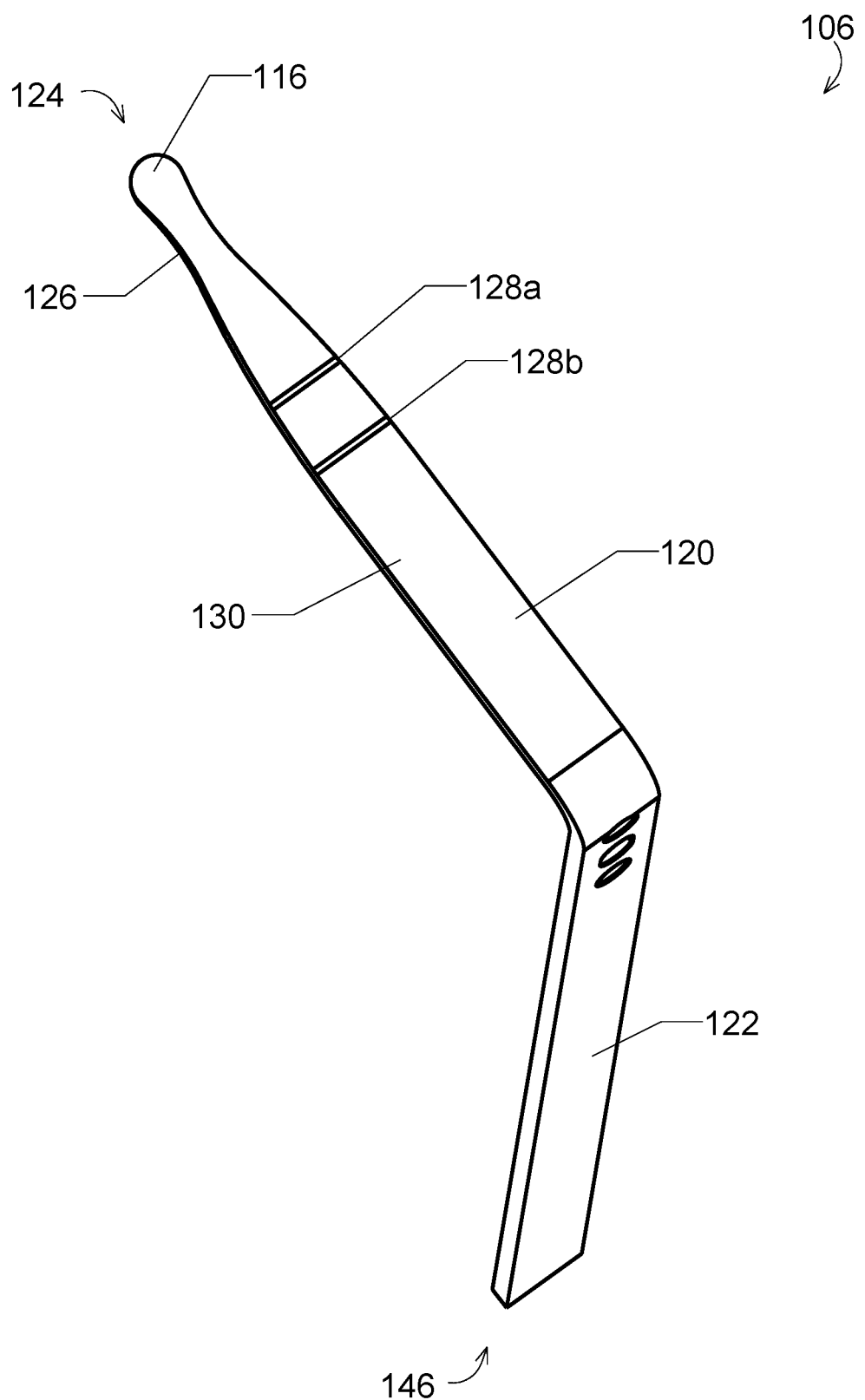
FIG. 4 is a perspective view of an anterior retractor of the surgical instrument system of FIG. 1.

FIGS. 4-7A disclose anterior retractors according to exemplary embodiments for use with the surgical instrument system 100 of the instant disclosure, which includes a lateral retractor shaft 120 extending from the tip 116, and a medial retractor shaft 122 extending substantially transverse from the lateral retractor shaft. The tip 116 in the embodiment shown in FIG. 4 contains an end 124 that is rounded and also tapered in width to provide a relatively pointed end, though alternatively the end 124 can include a forked end, a pointed end, or other shape or configuration suitable for its intended purpose. A neck 126 having a width less than a width at the tip 116, and a width less than a width of the lateral retractor shaft 120, extends between the tip and the lateral retractor shaft 120. A pair of indicia 128a, 128b (e.g., transverse markings) can optionally be provided on a superior-facing face 130 of the lateral retractor shaft. These markings 128a, 128b can correspond to an anatomical distance from the end 124 of the tip 116, such as the distance from an anterior neck of the glenoid 132 to the outer perimetry of the glenoid cavity 134 for a typical female (128a) and male (128b) subject (FIGS. 2-4).

Figure 5:
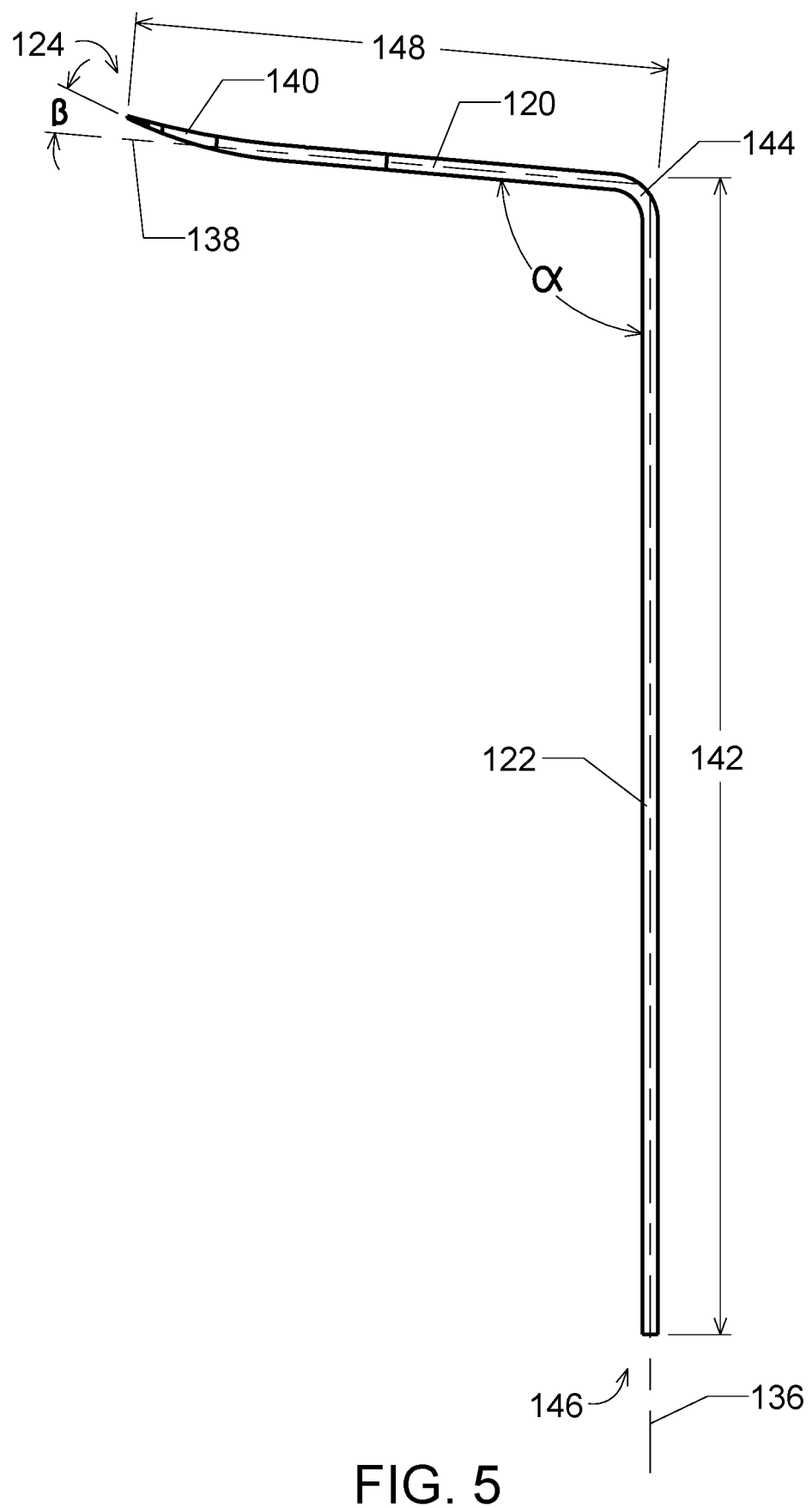
FIG. 5 is a side view of the anterior retractor of FIG. 4.

With reference to FIG. 5, the medial retractor shaft 122 has a length 142 (e.g., 220 mm) from a junction 144 to a proximal end 146 of the medial retractor shaft. The lateral retractor shaft has a second length 148 (e.g., 100 mm) from the junction 144 to the end 124 of the tip 116. In this exemplary embodiment, the length 142 of the medial retractor shaft is at least twice (e.g., at least a multiple of 2.1, or about 2.2) the length 148 of the lateral retractor shaft, though other dimensioning can be provided. For example, the length 142 can be 180, 190, 200, 210, 230, 240, or 250 mm, and the second length 148 can be 80, 90, 110, or 120 mm.

Longitudinal axis 136 of the medical retractor 122 extends at an angle α from longitudinal axis 138 of the lateral retractor shaft 120. In this exemplary embodiment, the angle α can range from about 90 degrees to about 110 degrees (e.g. 80, 100, and 110 degrees). Starting, for example, slightly distal to the neck 126, the lateral retractor shaft 120 includes a superior flare 140 that extends in a superior direction at an angle β from longitudinal axis 138, that can range, for example, from about 1 degree to about 35 or 40 degrees (e.g., 2, 5, 7, 10, 12, 17, 20, 22, 25, 27, 30, 38, 42 degrees), extending a distance 135 in the superior direction (FIG. 6), both being provided to allow clearance of anterior/interior edge of the glenoid. In exemplary embodiments, ratio of the (distance 148 from the junction 144 to the end 124 of the tip 116):(distance 135) is from about 15:1 to about 20:1 (e.g., about 17-18), though other dimensioning can be provided in alternative embodiments.

Figure 6:
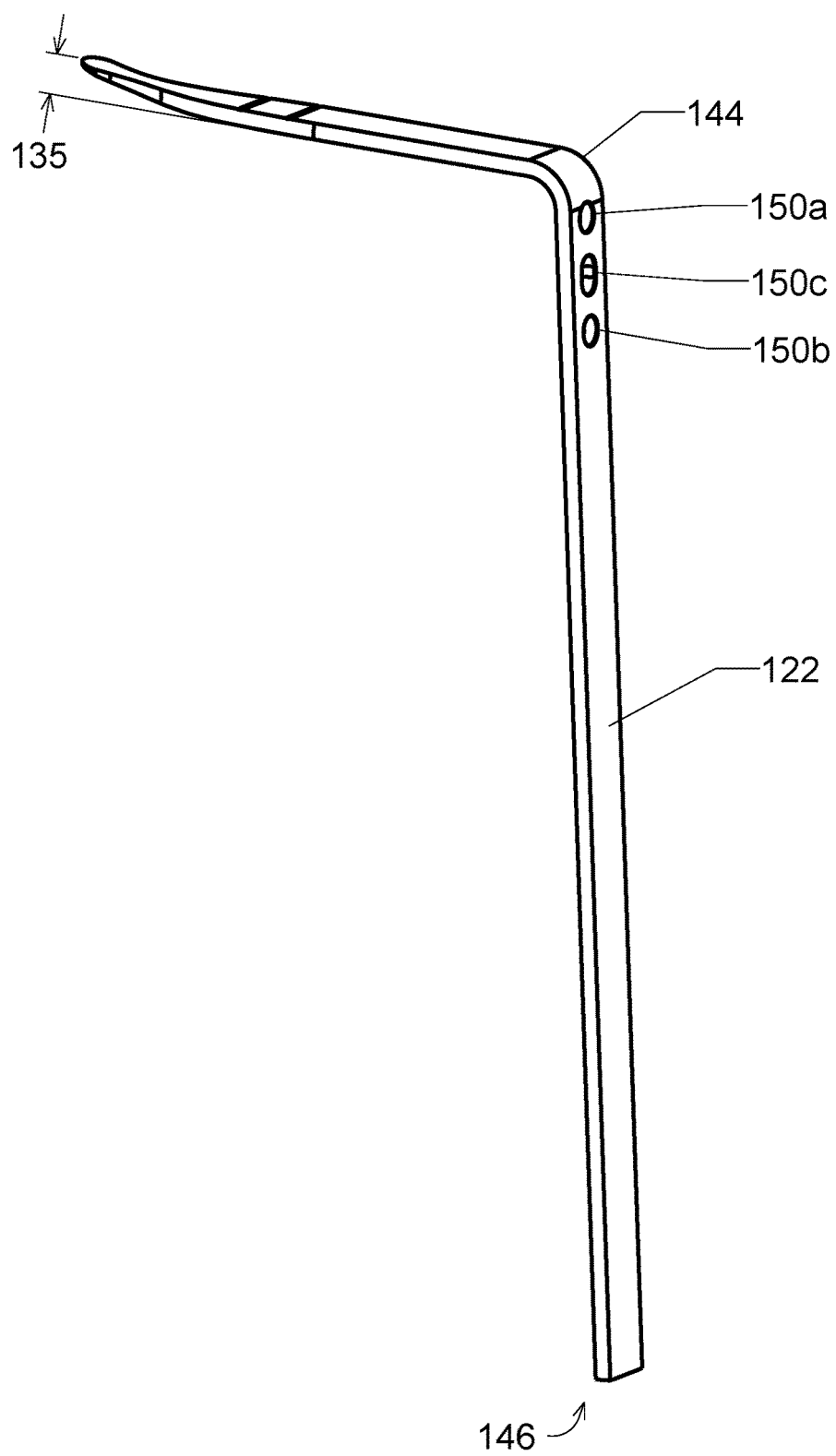
FIG. 6 is another perspective view of the anterior retractor of FIG. 1.

With reference to FIG. 6, the medial retractor shaft 122 includes a receiving portion which in this embodiment is in the form of through holes 150a-150c. In this particular embodiment, through holes 150a, 150b have a circular cross-sectional shape whereas through hole 150c has an oval cross-sectional shape. Each through hole is sized to receive counterparts from a fastener 152 associated with the alignment guide 108, discussed below, to secure the alignment guide to the anterior retractor 106 in a lockable and unlockable manner, e.g., between a locked and unlocked position.

Figure 7:
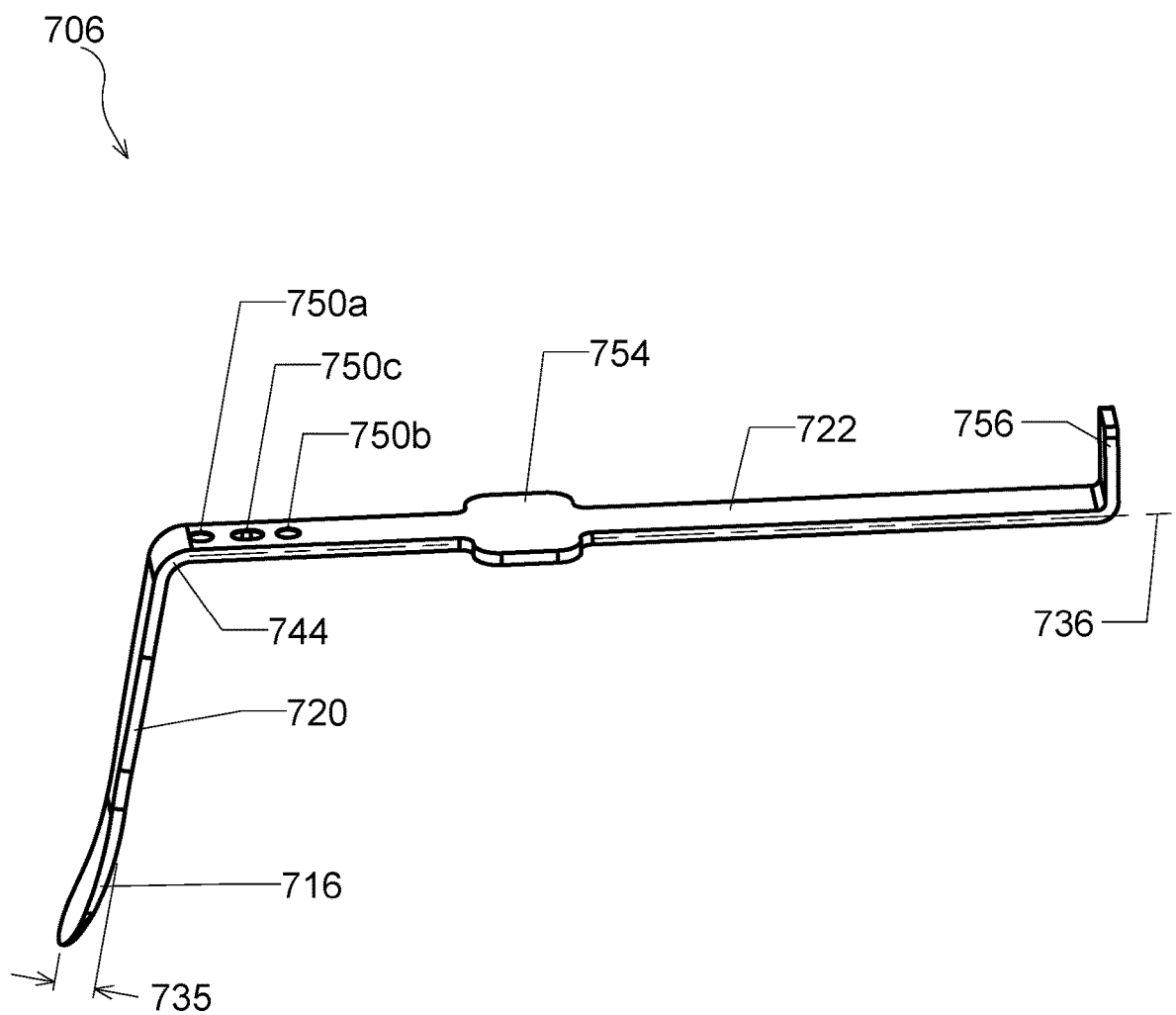
FIG. 7 is a perspective view of an anterior retractor in accordance with another exemplary embodiment of the subject disclosure.
Figure 7A:
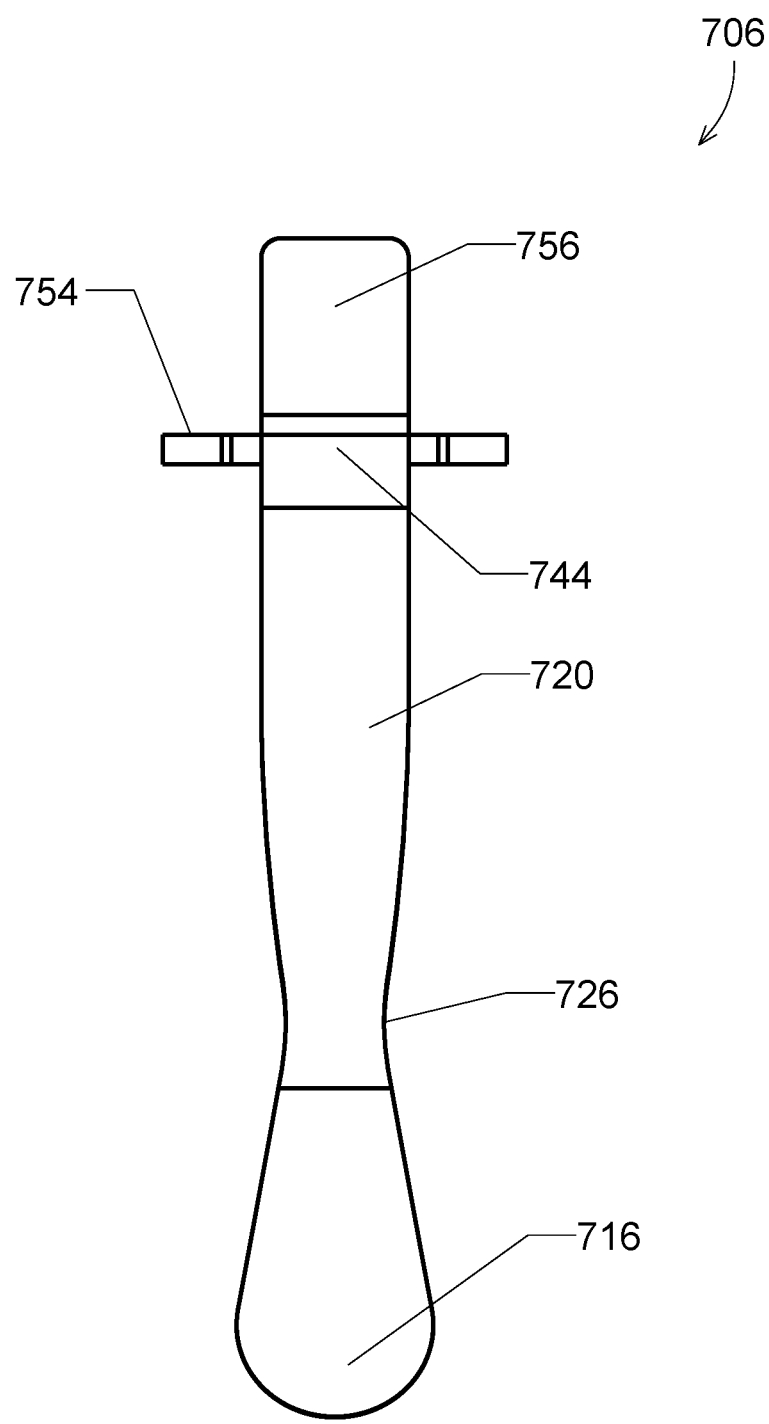
FIG. 7A is a top plan view of the anterior retractor of FIG. 7.

FIGS. 7 and 7A disclose an anterior retractor 706 according to another exemplary embodiment that can be used in the surgical instrument system 100 of the subject disclosure. Anterior retractor 706, except as noted below, is similar in structure to anterior retractor 106 and similarly includes a tip 716, lateral retractor shaft 720, junction 744, through holes 750a, 750b, 750c and medial retractor shaft 722. Shown best in FIG. 7A, the anterior retractor also includes a neck 726 having a width (e.g., 10 mm) less than a width of the lateral retractor shaft (e.g., 15 mm), and also less than a width at the tip 716. For example, the width of the neck 726 can be a multiple of 0.5, 0.67, 0.75, or 0.8 of the width of the lateral retractor shaft 720. In similar fashion to anterior retractor 135, the lateral retractor shaft 720 includes a superior flare that extends a distance 735 in the superior direction. While anterior retractor 706 is dimensioned similar to anterior retractor 106, other dimensions can be provided in alternative embodiments.

Anterior retractor 706 further includes a manual indicia of position 754, which in this embodiment in the form of a segment with increased width, though other configurations can be provided to facilitate manual manipulation and to allow an operator to manually ascertain when he or she is approaching the junction 144. The anterior retractor further includes a second lateral retractor shaft 756 extending, in this exemplary embodiment, at about a right angle from a longitudinal axis 736 defined by the medial retractor shaft 722, though it can alternatively extend at other angles, e.g., 80 and 100 degrees.

Figure 8:
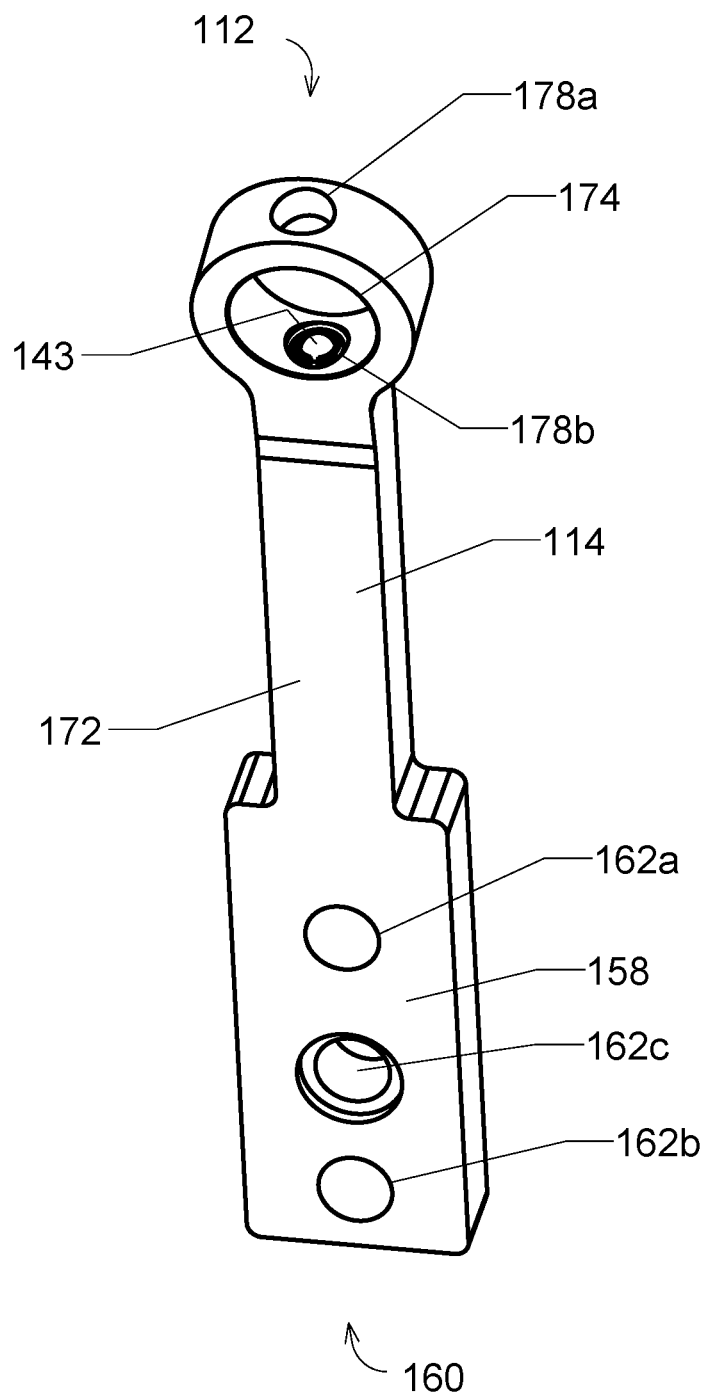
FIG. 8 is a perspective view of an alignment guide shaft and guide aperture of the surgical instrument system of FIG. 1.
Figure 9:
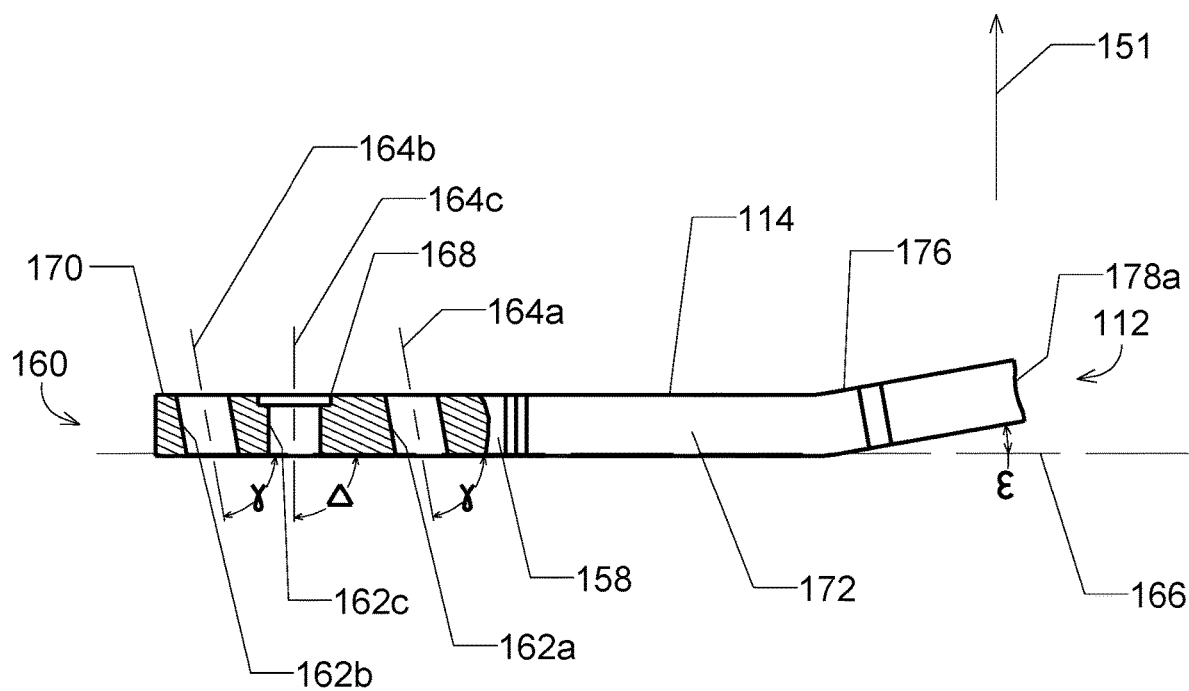
FIG. 9 is a side view of the alignment guide shaft and guide aperture of FIG. 8.

FIGS. 8-9 disclose components of the alignment guide 108 which includes an alignment guide shaft, a guide, and a fastener. The alignment guide shaft 114 has a longitudinal axis 166 and further includes an engagement segment 158 of relatively higher width about a proximal end 160 of the alignment guide shaft coupled to its distal end. The engagement segment 158 includes through holes 162a, 162b, 162c adjacent the proximal end 160, each through hole defining respective longitudinal axes 164a, 164b and 164c. Through holes 162a, 162b can be sized to receive dowel pins 137a, 137b (e.g., 5 mm dowel pins) that can be press jolted or otherwise permanently fixated therein for engagement with through holes 150a, 150b. Through hole 162c, like through hole 150c, is sized to engage the fastener 152.

In this exemplary embodiment, through holes 162a, 162b extend obliquely at an angle γ, from the longitudinal axis 166 of from about 91 degrees to about 110 degrees (e.g., 92, 94, 96, 98, 100, 102, 104, 106, and 108 degrees) and through hole 162c is cut substantially perpendicular to the longitudinal axis at an angle, Δ that is, for example, from about 85 degrees to about 95 degrees (e.g., 90, 93, 97 degrees). Other dimensioning can be provided in alternative embodiments. Through hole 162c includes a circular flange-like counter sink 168 of increased diameter about an anterior-facing face 170 of the alignment guide shaft 114.

The alignment guide shaft 114 includes a segment 172 of narrower width compared to the distal end extending from the engagement segment 158, and extends to a guide aperture 174 about the distal end 112 of the alignment guide shaft 114. As shown best in FIG. 9, the alignment guide shaft 114 includes a lateral flare 176 such that the guide aperture 174 extends at an angle ε from the longitudinal plane 166 of the alignment guide shaft 114, which in this exemplary embodiment can range, for example, from about 1 degree to about 20 degrees (e.g., 2, 4, 6, 8, 10, 12, 14, 16, and 18 degrees) in a medial direction 151. The lateral flare 176, i.e., flares laterally extends to a guide aperture 174 that defines a circular cross-sectional shape with an aperture diameter that can range, for example, from about 5 mm to about 15 mm (e.g., 5, 6, 7, 8, 9, 10, 11, 12, 13, and 14 mm), though other dimensioning can be provided.

Figure 8A:
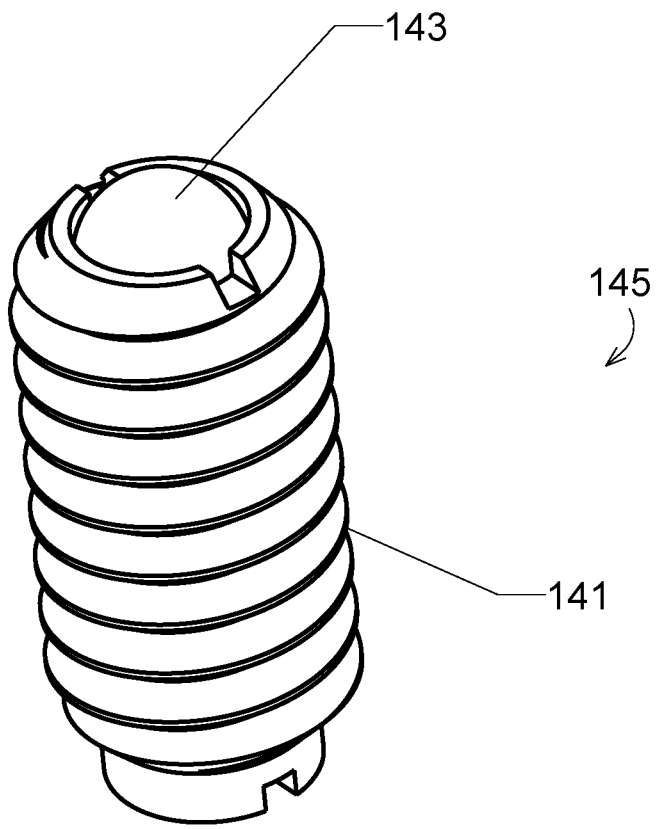
FIG. 8A is a perspective view of a ball plunger for use with the alignment guide shaft and guide aperture of FIG. 8.

The guide aperture 174 includes through holes 178a, 178b traversing the guide aperture 174 as shown in FIG. 8. The through hole 178b is threaded and sized to receive a ball plunger 145, as best shown in FIGS. 8A and 10A. The ball plunger 145 includes a biased ball detent 143 and threads 141 complimentary to the threads in threaded hole 178b. Access to through hole 178b is provided by through hole 178a. Ball detent can be sized to engage grooves 159b, 159c of a guide pin cannula 169, discussed below.

Figure 10:
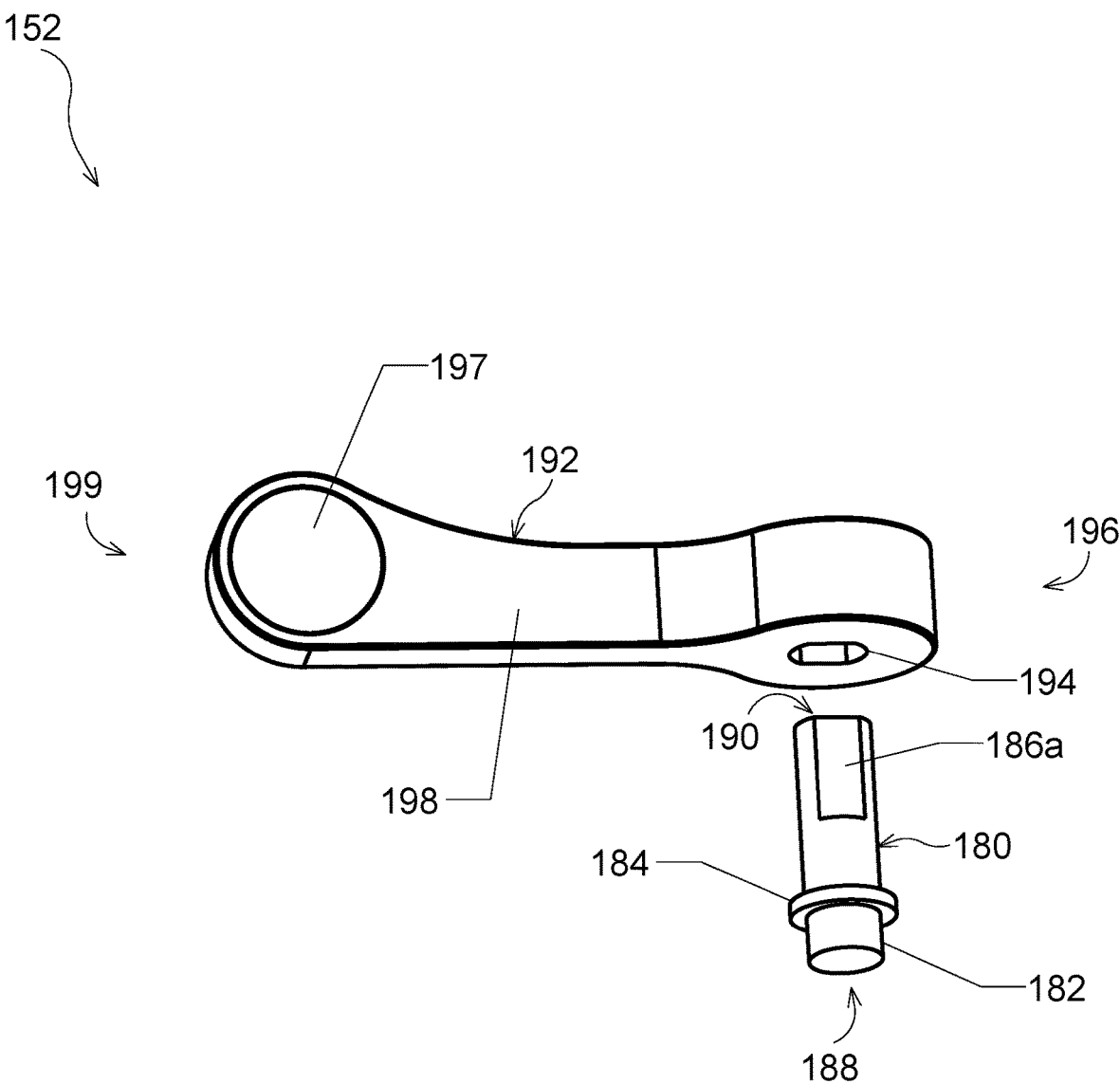
FIG. 10 is a perspective view of a fastener of the surgical instrument system of FIG. 1.
Figure 10A:
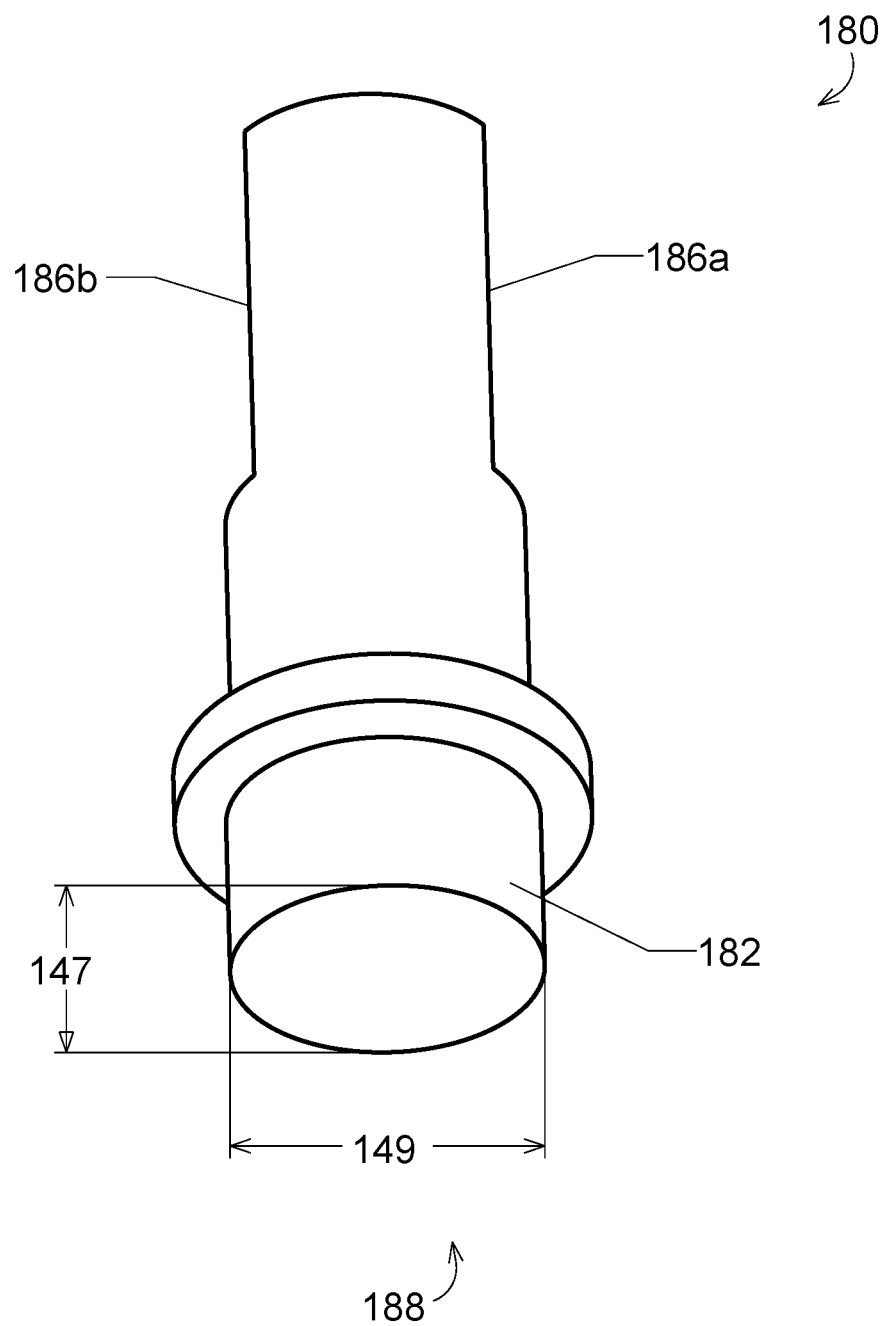
FIG. 10A is a perspective view of a cam pin for use with the fastener of FIG. 10.

FIG. 10 discloses the fastener 152, which in this exemplary embodiment is in the form of a cam lock capable of connecting the alignment guide shaft 114 to the anterior retractor 106 to reversibly lock and unlock the alignment guide shaft to the anterior retractor. Alternatively, other fasteners can be employed in place of a cam lock to secure the alignment guide 108 to the anterior retractor 106.

Figure 10B:
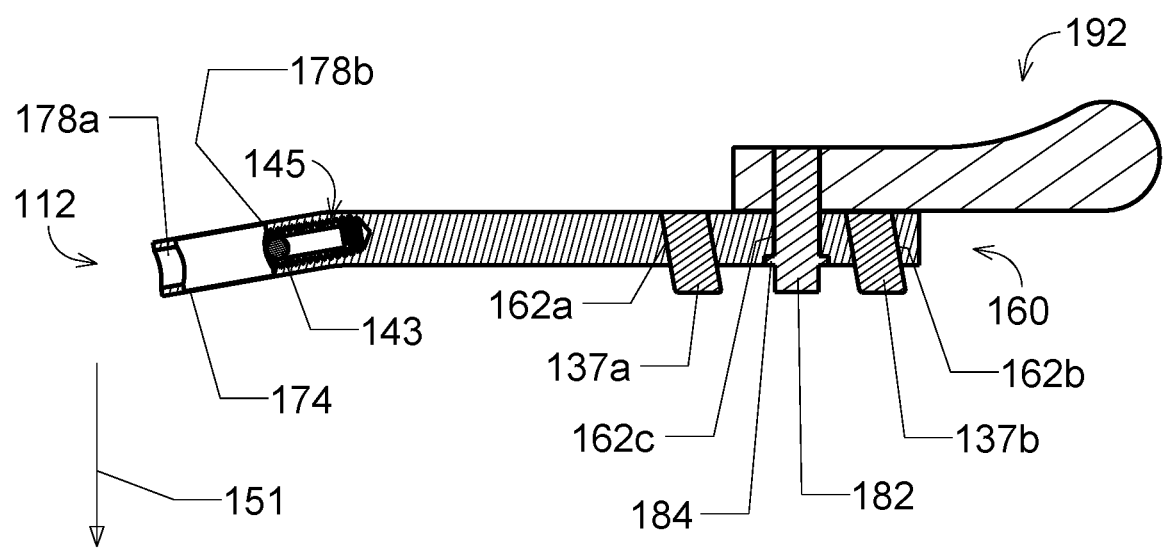
FIG. 10B is a cross-sectional view of the alignment guide shaft and guide aperture of FIG. 8 engaged with the fastener of FIG. 10.

With reference to FIGS. 10A-10B, the fastener 152 according to this exemplary embodiment includes a cam pin 180 that includes a plug 182 with an oval cross-sectional shape about an end 188 of the cam pin. For example, a major diameter 149 (e.g., 5.2 mm) of the plug can be about 1.1× or 1.2× a minor diameter 147 (e.g., 4.8 mm) of plug. The plug 182 is sized to be received by through hole 162c and through hole 150c and, when rotated a quarter turn such that the major diameter 149 of plug 182 is imposed upon the minor diameter of through hole 150c, to form an interference fit therewith. The plug 182 extends to a flange 184 shaped to be received by counter sink 168 of through hole 162c. A couple of diametrically opposed planar faces 186a, 186b are provided about its proximal end 190 of the cam pin 180 for fixedly engaging the thumb turn 192 and to allow the thumb turn to rotate the cam pin.

Thumb turn 192 is best shown in FIG. 10, and includes a thumb turn aperture 194 about its proximal end 196. The thumb turn aperture 194 includes a couple of flats 196a, 196b shaped to receive and engage with the planar faces 186a, 186b of the cam pin 180. A shaft 198 is provided between the proximal end 196 and the distal end 199. A thumb recess 197 is provided about the distal end of the thumb turn 192 to facilitate manual manipulation.

Figure 11:
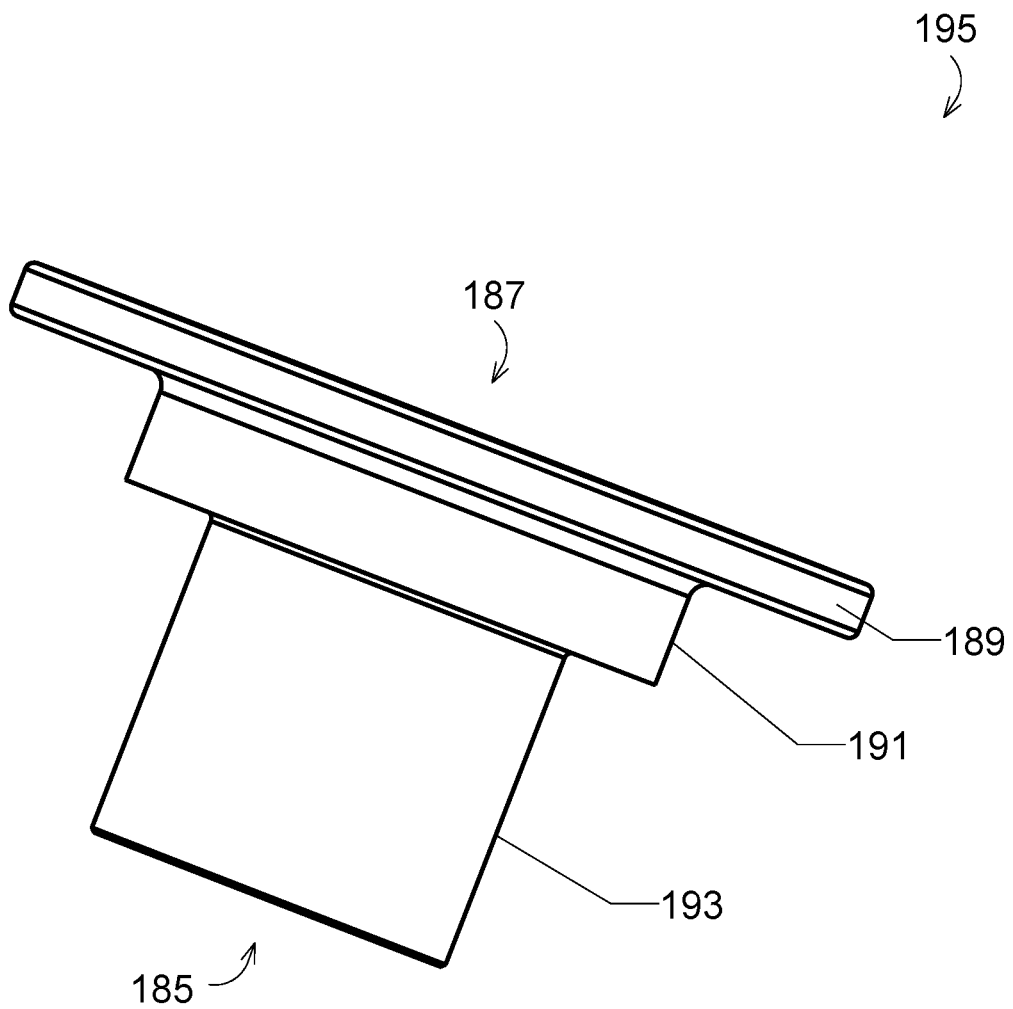
FIG. 11 is a perspective view of a guide insert of the surgical instrument system of FIG. 1.
Figure 12:
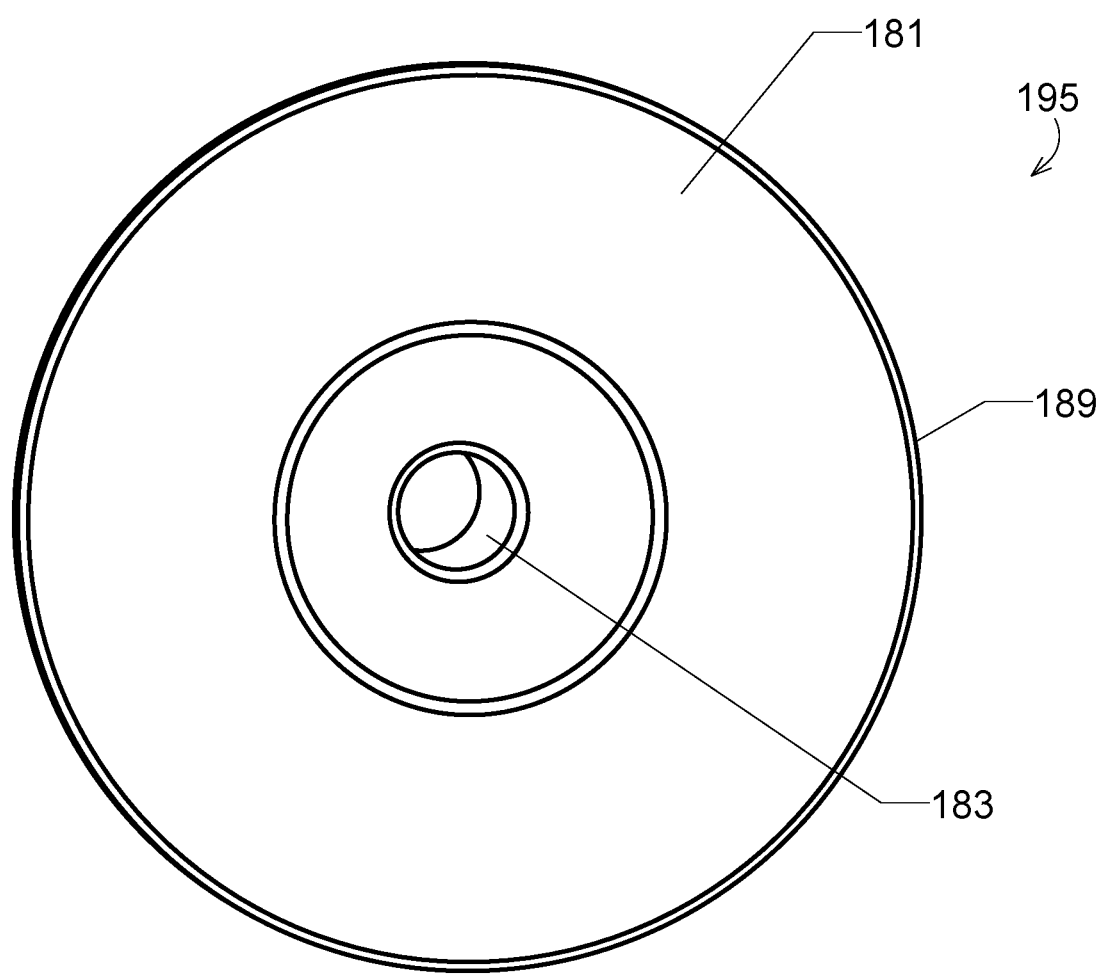
FIG. 12 is a plan view of the guide insert of FIG. 11.
Figure 13:
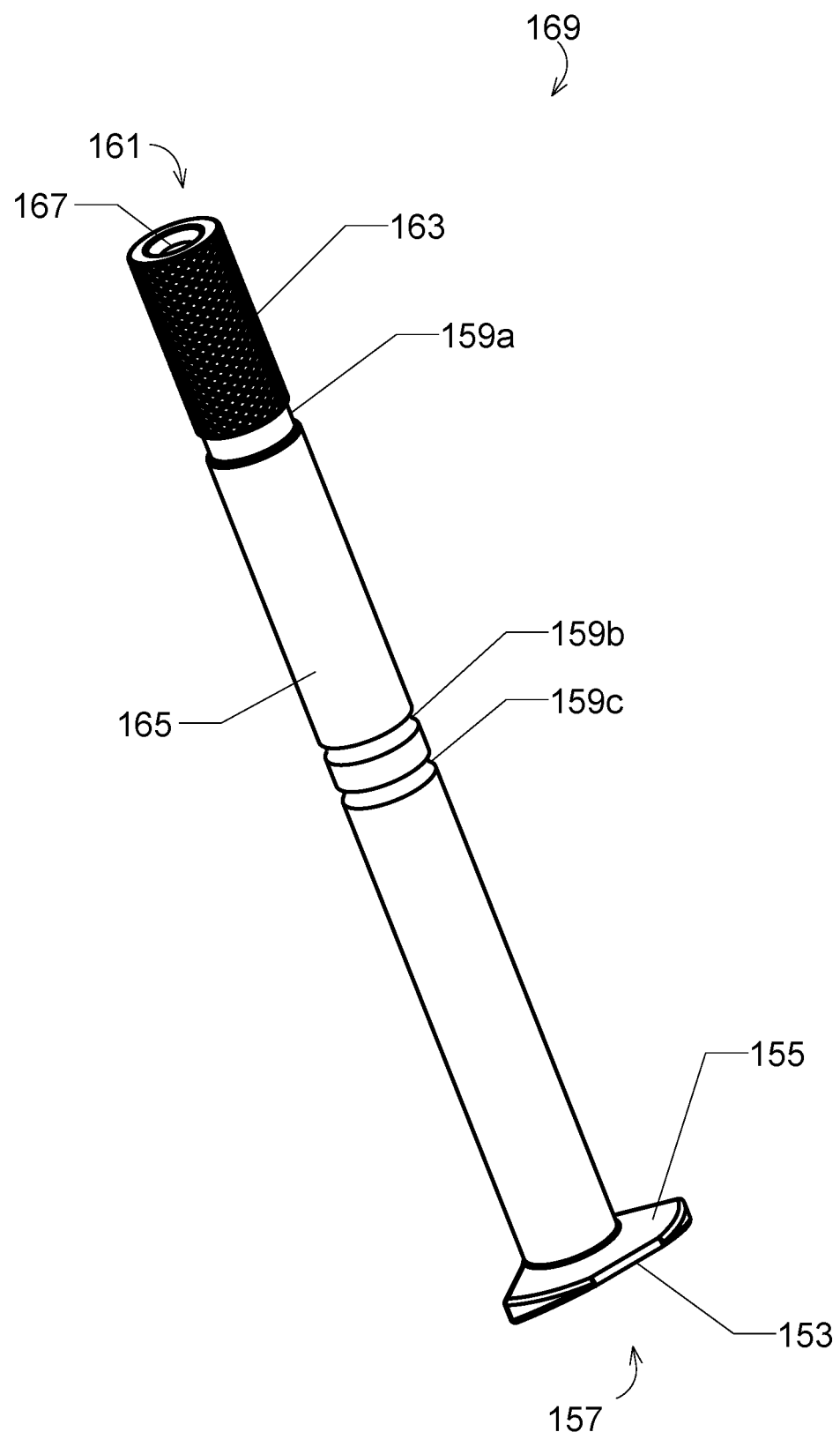
FIG. 13 is a guide pin cannula for use with the surgical instrument system of FIG. 1 according to an alternative embodiment.
Figure 13A:
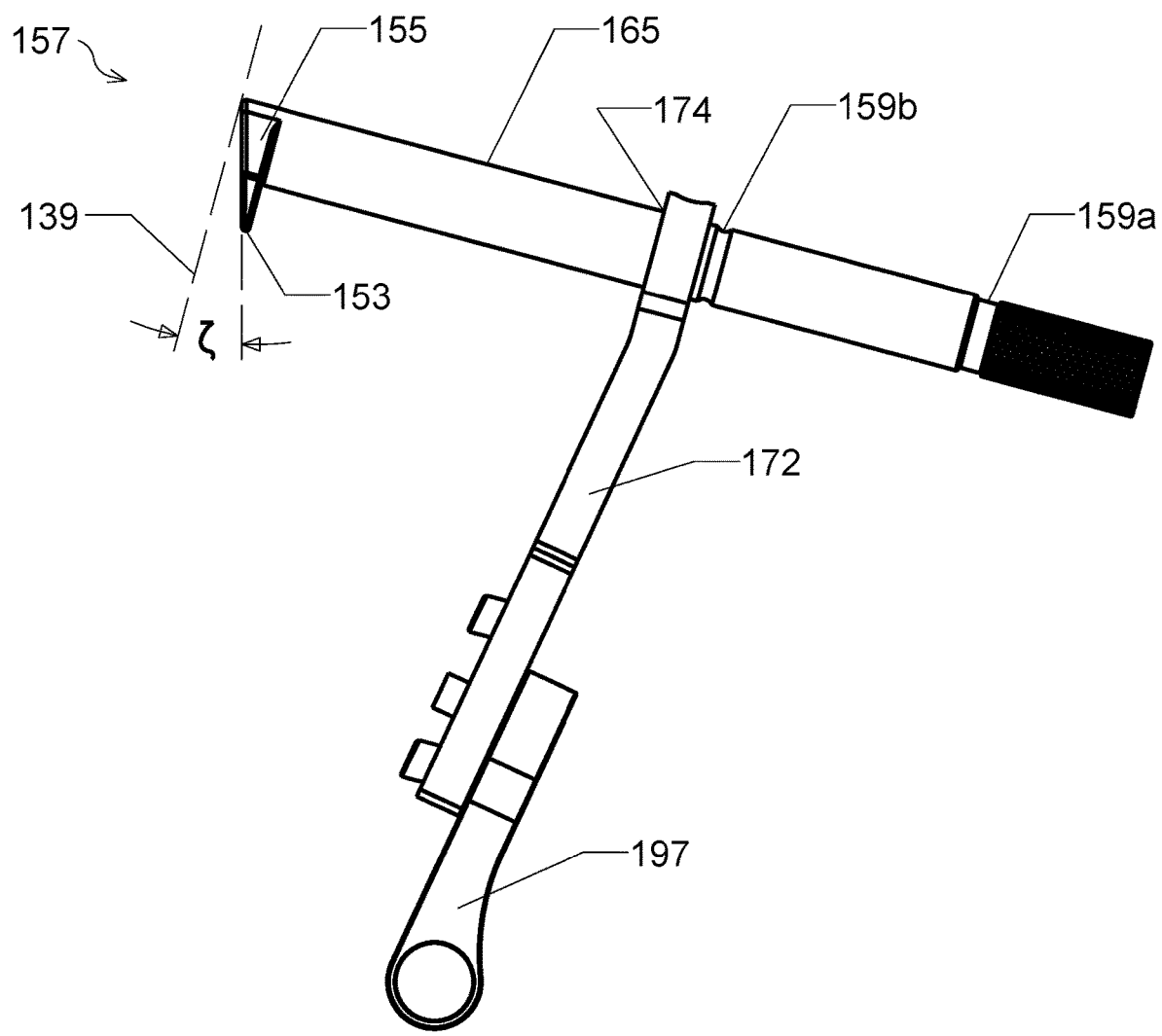
FIG. 13A is a perspective view of the alignment guide shaft and guide aperture of FIG. 8 engaged with the guide pin cannula of FIG. 13.
Figure 14:
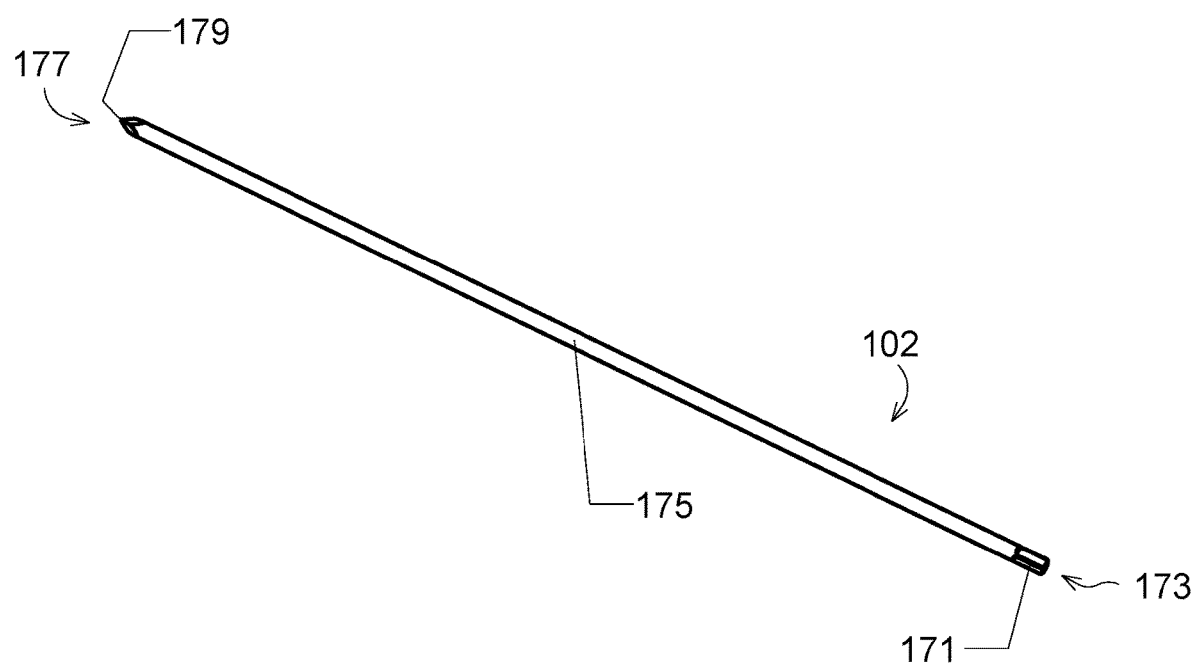
FIG. 14 is a guide pin of the surgical instrument system of FIG. 1.

The guide aperture 174 can be provided with a guide insert 195, as shown in FIGS. 11-12, or alternatively with a guide pin cannula 169, as shown in FIGS. 13-13A, to receive guide pin 177, as shown in FIG. 14.

In one exemplary embodiment, the guide 110 further includes the guide insert 195, that can be welded into the guide aperture 174. Alternatively, the guide insert 195 can be provided as a separate component. The guide insert 195, shown in FIG. 11 prior to welding, includes a hollow shaft 193 with an outer diameter sized to be received by the guide aperture 174. A flange 191 of greater outer diameter than the guide aperture 174 extends from the hollow shaft 193, and a collar 189 of a still greater outer diameter than the flange is provided about an end 187 of the guide insert.

With reference to FIG. 12, the hollow shaft 193 is provided with a longitudinally-elongated center inner through hole aperture 183. The inner aperture 183 is sized to receive the guide pin 102. The inner aperture 183 flares outward to provide an increasing diameter until it approaches a face 181 provided adjacent the collar 189, e.g., in a frustoconical manner. As shown in FIGS. 1-3, the guide insert 195 is spaced from the glenoid cavity 104

The guide pin cannula 169 is shown in FIGS. 13-13A, which can be provided as an alternative to guide insert 195. The guide pin cannula 169 includes an internal bore 167 sized to receive the guide pin 102. A diamond knurl 163 is provided about a proximal end 161 of the guide pin cannula. The cannula shaft 165 includes one or more grooves or annular recesses 159a, 159b, 159c along its longitudinal length. Grooves 159b and 159c are spaced to assist in anchoring the guide pin cannula 169 within the guide aperture 174 at the desired location along the longitudinal length of the cannula shaft 165. More particularly, in this exemplary embodiment, the grooves 159b and 159c are sized to engage the ball detent 143 and are spaced along the cannula shaft 165 such that a distal end 157 of the cannula will engage or substantially engage the glenoid cavity for anatomically-conventional men (159c) and women (159b), though the guide pin can be operated without benefit of the grooves when performing properly on subjects with atypical anatomy as needed to engage the glenoid cavity.

A quarter-circular flange 155 is provided about the distal end 157 of the guide pin cannula. The quarter-circular flange 155 includes a truncated face 153. As shown in FIG. 13A, the distal end 157 defines a plane 139 perpendicular to the cannula shaft 165. The flange 155 extends at an angle from the plane 139 that can range, for example, from about 5 to about 25 degrees (e.g., 15 degrees). After the distal end 157 engages the glenoid cavity 104, the flange can be made flush with the glenoid cavity, which in turn will orient the guide pin at an increased superior angle, which in turn will orient the glenosphere at increased inferior angle, which in turn can prevent scapular notching. The guide pin cannula can be pre-loaded loaded with a guide pin advanceable within the internal bore 167 and capable of penetrating the glenoid cavity.

The guide pin 102 is configured as best shown in FIG. 14 and includes a sharp tip 179 about a distal end 177 of the guide pin structured to penetrate a glenoid cavity, and a shaft 175 extending therefrom. A proximal end 173 of the guide pin is shaped to provide a fitting 171 compatible with a tool (not shown), such as a handle or drill, for advancing the guide pin.

Operation of the surgical instrument system 100 will now be described in greater detail, based on use of the guide pin cannula disclosed in FIGS. 13-13A. An operator advances the tip 116 of the anterior retractor between the subscapularis and the anterior neck of the glenoid. Placement of the tip 116 is facilitated by keeping tension on the subscapular tag suture during advancement of the tip. The tip 116 is maintained in contact with the anterior neck of the glenoid by sliding it in a posterior medial direction. The center of the inferior glenoid circle can be identified and marked with a Bovie™ or like instrument. The alignment guide 108 is then attached to the medial retractor shaft via through holes 150a, 150b, 150c, and the thumb turn 197 is rotated one quarter turn.

The alignment guide aperture 174 slidably houses the guide pin cannula 161, which in turn contains a guide pin advanceable therein. The guide pin cannula is advanced in a longitudinal direction through the guide pin aperture until the ball detent 143 engages either groove 159b or 159c, which should engage the distal end 157 of the cannula with the glenoid cavity 102 at the Bovie™ mark for anatomically conventional subjects. The flange 155 is then made flush with the glenoid cavity.

Alternatively, if a guide pin insert 195 is employed instead of guide pin cannula 161, the guide pin 102 can be advanced in a longitudinal direction through aperture 183 to penetrate the glenoid cavity at the Bovie™ mark.)

After the flange 155 is made flush with the glenoid cavity, the guide pin is advanced through the internal bore 167 of the guide pin cannula 161 (or inner aperture 183 of the guide pin insert 195) to penetrate the glenoid cavity and exit the far medial glenoid vault cortex just posterior to the tip 116 (see FIG. 2). When advancing the guide pin, the operator will feel two distinct cortices, once through the second cortex, advancement is halted. The alignment guide 108 is then detached from the anterior retractor 106 by turning the thumb turn 197 back to its original position and sliding the alignment guide 108 off over the guide pin. As the tip 116 maintains contact with the anterior neck of the glenoid throughout the entire process, the system 100 serves a dual purpose of retraction (via, e.g., the lateral retractor shaft 120 and the medial retractor shaft 122) and guiding the guide pin.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

The invention claimed is:

1. A surgical instrument system for positioning a guide pin about a glenoid cavity comprising:
   an anterior retractor that includes:
      a tip structured to engage a scapula,
      a lateral retractor shaft extending from the tip, and
      a medial retractor shaft extending substantially transverse from the lateral retractor shaft; and
   an alignment guide attachable to the anterior retractor, the alignment guide including:
      an alignment guide shaft,
      a guide about a distal end of the alignment guide shaft, and
      a fastener for connecting the alignment guide shaft to the anterior retractor such that a longitudinal axis of the alignment guide shaft is aligned with a longitudinal axis of the medial retractor shaft when fastened thereto.

2. The surgical instrument system of claim 1, wherein the medial retractor shaft extends from the lateral retractor shaft at an angle of about 90 to about 110 degrees.

3. The surgical instrument system of claim 1, wherein the medial retractor shaft extends from the lateral retractor shaft at an angle of about 100 degrees.

4. The surgical instrument system of claim 1, wherein the tip comprises a superior flare or curvature.

5. The surgical instrument system of claim 1, wherein the medial retractor shaft extends a length at least twice a length of the lateral retractor shaft.

6. The surgical instrument system of claim 1, wherein the medial retractor shaft includes a manual indicia of position along the lateral retractor shaft.

7. The surgical instrument system of claim 1, wherein the medial retractor shaft includes at least one through hole for engaging the fastener.

8. The surgical instrument system of claim 1, wherein the alignment guide is attachable to the anterior retractor adjacent a junction of the lateral retractor shaft and the medial retractor shaft.

9. The surgical instrument system of claim 1, wherein the lateral retractor shaft includes a marking about an outer periphery a pre-determined distance from the tip corresponding to a distance from an anterior neck of a glenoid to an outer periphery of the glenoid cavity.

10. The surgical instrument system of claim 1, wherein the anterior retractor further comprises a second lateral retractor shaft extending from the medial retractor shaft.

11. The surgical instrument system of claim 1, wherein the fastener is a cam lock.

12. The surgical instrument system of claim 1, wherein the alignment guide shaft includes at least one through hole with a longitudinal axis therethrough that extends at an angle from about 90 degrees to about 110 degrees from a longitudinal axis of the alignment guide shaft.

13. The surgical instrument system of claim 1, wherein the guide includes a guide aperture about the distal end of the alignment guide shaft.

14. The surgical instrument system of claim 13, wherein the guide aperture extends at an angle of from about 1 degrees to about 20 degrees from a longitudinal axis.

15. The surgical instrument system of claim 13, further comprising a biased detent about the guide aperture.

16. The surgical instrument system of claim 1, further comprising a guide pin cannula receivable by the guide.

17. The surgical instrument system of claim 16, wherein the guide pin cannula comprises a distal tip that includes a flange.

18. The surgical instrument system of claim 17, wherein the flange extends at an angle of from about 5 to about 25 degrees from a plane perpendicular to a guide pin cannula shaft.

19. The surgical instrument system of claim 16, wherein the guide pin cannula includes a guide pin advanceable therein.

20. The surgical instrument system of claim 1 further comprising a guide insert including an inner aperture sized to receive a guide pin.

* * * * *